United States Patent [19]

Barton et al.

[11] Patent Number: 4,668,356

[45] Date of Patent: May 26, 1987

[54] PHOTOLYTIC PROCESS FOR THE FORMATION OF CARBON-CONTAINING FREE RADICALS AND ITS APPLICATIONS TO FREE RADICAL POLYMERIZATION IN PARTICULAR

[75] Inventors: Derek H. R. Barton, Gif sur Yvette; David Crich, Bures; William B. Motherwell, Gif sur Yvette, all of France

[73] Assignee: Centre National de la Recherche Scientifique (CNRS), Paris, France

[21] Appl. No.: 643,178

[22] Filed: Aug. 22, 1984

[30] Foreign Application Priority Data

Aug. 23, 1983 [FR] France .............................. 83 13598

[51] Int. Cl.$^4$ ............................................. B01J 19/12
[52] U.S. Cl. .......................... 204/157.6; 204/157.71; 204/157.77; 204/157.87; 522/189
[58] Field of Search .......... 204/157.6, 157.77, 157.69, 204/157.87, 157.71; 522/50, 189; 526/89

[56] References Cited

U.S. PATENT DOCUMENTS 3,227,698  1/1966  Robinson ..................... 204/157.6
3,276,982  10/1966  Barton ........................ 204/157.77

OTHER PUBLICATIONS

Horner et al. –Chemical Abstracts vol. 52, No. 2, Jan. 10, 1958, column 284(c).

*Primary Examiner*—Howard S. Williams

*Attorney, Agent, or Firm*—Dressler, Goldsmith, Shore, Sutker & Milnamow, Ltd.

[57] ABSTRACT

Process for the formation of carbon-containing free radicals R., which optionally include functional groups, wherein thermal and/or photochemical energy is supplied to a thiocarbonyl-containing ester corresponding to the general formula (I):

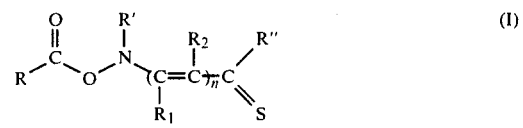

in which:

R denotes a saturated or unsaturated, linear or branched, aliphatic or aromatic, acyclic or alternatively mono- or poly-cyclic or mono- or poly-heterocyclic, carbon-containing radical which in addition can optionally include functional groups;

R' and R" denote, independently of each other, an alkyl, alkenyl, aryl, aralkyl or alkaryl radical, or alternatively form together a 5- or 6-membered nitrogen-containing heterocycle which can also contain an additional heteroatom chosen from nitrogen and sulfur and which can optionally be substituted or fused to at least one other aliphatic or aromatic ring;

$R_1$ and $R_2$ denote, independently of each other, a hydrogen atom or a lower alkyl radical, and n is an integer equal to 0, 1, 2 or 3.

7 Claims, No Drawings

PHOTOLYTIC PROCESS FOR THE FORMATION OF CARBON-CONTAINING FREE RADICALS AND ITS APPLICATIONS TO FREE RADICAL POLYMERIZATION IN PARTICULAR

The present invention relates to a process for the formation of carbon-containing free radicals R. which optionally include functional groups and which bear their free electron on a carbon atom.

In recent years, free radical reactions have developed greatly in the general field of organic synthesis. These free radical reactions have in fact a number of significant advantages relative to the more conventional ionic reactions. First, free radical chain reactions can generally be conducted under neutral conditions. In addition, these reactions are performed under very mild conditions, which makes it possible to avoid interference of a steric or polar nature occurring with the starting materials. Furthermore, this type of reaction is generally not accompanied by spurious reactions of carbocationic rearrangement or carbanionic elimination.

The present invention therefore had the object of perfecting a new process for the formation of carbon-containing free radicals, the functionality of which is unmodified relative to the starting materials. The process of the invention consists essentially of a free radical decarboxylation of esters of organic acids which can be primary, secondary or tertiary. The mild conditions for carrying out this process have enabled excellent yields to be obtained of free radicals which retain, in particular, the ester, ketone and olefin functions of the starting material.

According to the present invention, the carbon-containing free radicals R., optionally including functional groups, are obtained by supplying thermal and/or photochemical energy to a thiocarbonyl-containing ester corresponding to the general formula (I):

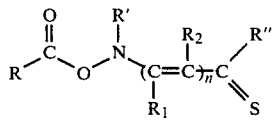
(I)

in which:
R denotes a saturated or unsaturated, linear or branched, aliphatic or aromatic, acyclic or alternatively mono- or poly-cyclic or mono- or poly-heterocyclic carbon-containing radical which in addition can optionally include functional groups;
R' and R" denote, independently of each other, an alkyl, alkenyl, aryl, aralkyl or alkaryl radical, or alternatively form together a 5- or 6-membered nitrogen-containing heterocycle which can also contain an additional heteroatom chosen from nitrogen and sulfur and which can optionally be substituted or fused to at least one other aliphatic or aromatic ring;
$R_1$ and $R_2$ denote, independently of each other, a hydrogen atom or a lower alkyl radical, and
n is an integer equal to 0, 1, 2 or 3.

According to an additional characteristic of the present invention, the said thiocarbonyl-containing ester is brought to a temperature which is substantially between 20° and 200° C., and preferably between 70° and 120° C.

The supply of photochemical energy is generally necessary when working within the ranges of low temperatures, for example below approximately 40° C. Whatever the temperature employed, the supply of additional photochemical energy leads to an increase in the rate of reaction. This photochemical energy can be supplied to the reaction medium containing the said thiocarbonyl-containing ester by luminous irradiation, in particular with visible light.

By way of illustration of the thiocarbonyl-containing esters of general formula (I) which can be employed within the scope of the present invention, there will be mentioned the following non-limitative examples corresponding to the following formulae:

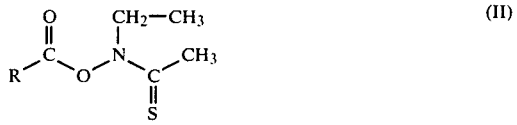
(II)

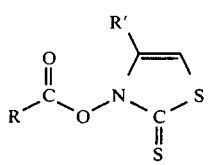

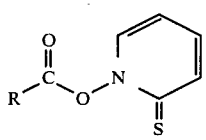

where R and R' have the significance given previously in relation to the general formula (I) and R' is preferably Me, H or Ph, for example.

These various thiocarbonyl-containing esters can be prepared by conventional synthesis processes. Within the scope of the present invention, the thionopyridone esters of general formula (II) can, however, be advantageously prepared by reaction of a free carboxylic acid of general formula (III):

$$RCO_2H \qquad (III)$$

in which R has the significance given in relation to the formula (I), with a compound of formula (IV):

(IV)

the latter being obtained by reaction of phosgene with N-hydroxypyridine-2-thione.

The thionopyridone ester of formula (IL) can also be prepared under excellent conditions by reaction of the mixed anhydride of general formula (V)

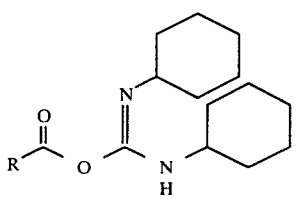

in which R has the significance given above, with N-hydroxy-pyridine-2-thione in the presence of a catalyst such as p-dimethylaminopyridine.

Finally, the thionopyridone ester of formula (II) can be obtained by reaction of an acid chloride of general formula (VI):

in which R has the significance given in relation to the formula (I), with the sodium salt of N-hydroxypyridine-2-thione, in the presence of a catalyst such as p-dimethyl-aminopyridine.

These three methods of preparation are summarized in the reaction scheme shown below:

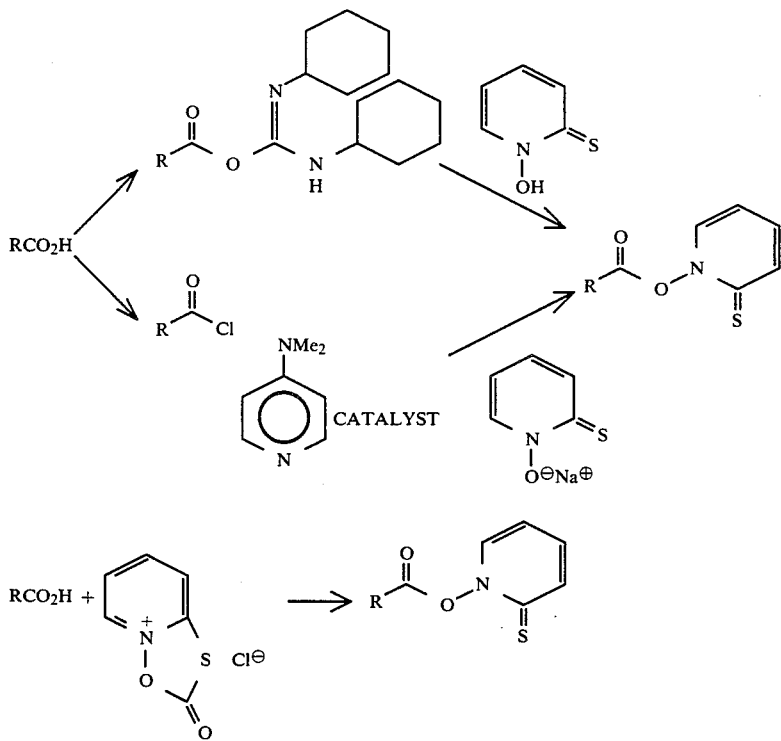

The present invention also extends to the preparation of a number of decarboxylated derivatives of the general formulae R—X or R—A—B—X.

The present invention relates, in particular, to a process for the preparation of a compound of general formula R—X starting from a carboxylic acid of general formula R—CO$_2$H, in which R has the significance given in relation to the formula (I), in which process there is added to the reaction medium for the formation of carbon-containing free radicals R. a compound of general formula X—Y, in which X, which denotes the group to be grafted onto the carbon-containing free radical R., is chosen from the hydrogen, chlorine, bromine and iodine atoms, and the like, and Y denotes a chain-bearing group chosen from n—Bu$_3$S., tert—BuS., CCl$_3$., CHI$_2$., R$_3$Sn., ArSO$_2$. and the like.

The invention also relates to a process for the preparation of a compound of general formula R—A—B—X from a carboxylic acid of general formula R—CO$_2$—H, in which R has the significance given for the formula (I), in which process, in addition to the compound of formula X—Y defined above, there is added to the reaction medium for the formation of carbon-containing free radicals R. a compound of general formula A=B chosen from oxygen, compounds with ethylenic unsaturation and azo derivatives.

It is useful to note that, by reaction with a single ethylenic monomer A=B, the process of the invention leads to a simple elongation of the carbon chain of the starting acid with a concomitant decarboxylation. In the presence of several monomers, the process finds application in free radical polymerization, especially ethylenic polymerization. Given that the thiocarbonyl-containing esters of formulae (I) and (II) are completely soluble in alkalis, they can be removed without difficulty when they are present in excess in the polymerization reaction medium. The general formation process of the carbon-containing free radicals R. is schematized below in relation to the particular thionopyridone ester of formula (II), in order to make it easier to understand:

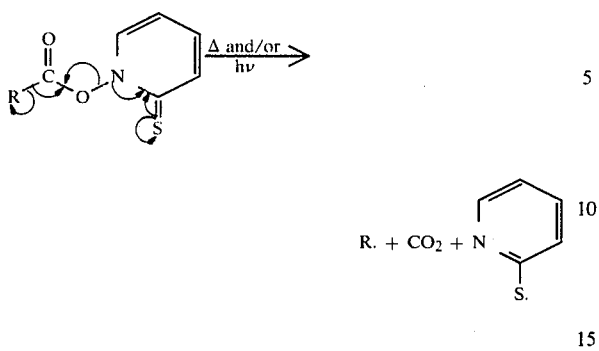

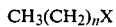

SCHEME 1

The process naturally remains the same in the case of the thiocarbonyl-containing ester of formula (I), by transfer along the olefin chain.

As mentioned above, the thiocarbonyl-containing ester which forms the free radicals R. is obtained from primary, secondary or tertiary carboxylic acids. By way of illustration, a few examples are shown below of acids which have been employed in practice. These acids are designated below by their general formula and are followed by various derivatives obtained within the scope of the present invention. These compounds are referred to by a number of brackets, which will be retained for identifying them in the remainder of the description.

PRIMARY ACIDS $CH_3(CH_2)_n X$

| | |
|---|---|
| n = 14; X = $CO_2H$ | (1) |
| n = 14; X = H | (2) |

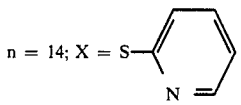

(3)

| | |
|---|---|
| n = 14; X = Cl | (4) |
| n = 14; X = Br | (5) |
| n = 14; X = I | (6) |
| n = 16; X = $CO_2H$ | (7) |
| n = 16; X = H | (8) |

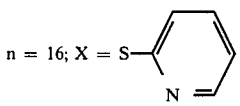

(9)

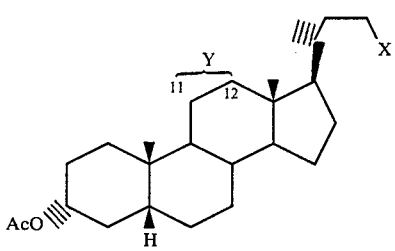

| | |
|---|---|
| Y = 12-oxo; X = $CO_2H$ | (10) |
| Y = 12-oxo; X = H | (11) |
| Y = 11-oxo; X = $CO_2H$ | (12) |
| Y = 11-oxo; X = H | (13) |

-continued
PRIMARY ACIDS

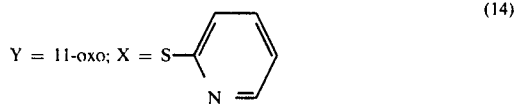

(14)

| | |
|---|---|
| Y = 11-oxo; X = Br | (15) |
| Y = 12 α-acetoxy; X = $CO_2H$ | (16) |
| Y = 12 α-acetoxy; X = H | (17) |

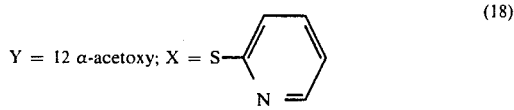

(18)

Y = 12 α-acetoxy; X = Cl (19)

(X = $CO_2H$)

SECONDARY ACIDS

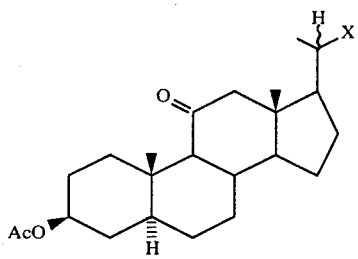

| | |
|---|---|
| X = $CO_2H$ | (20) |
| X = H | (21) |

(22)

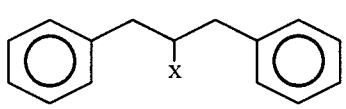

| | |
|---|---|
| X = $CO_2H$ | (23) |
| X = H | (24) |

(25)

| | |
|---|---|
| X = Cl | (26) |
| X = Br | (27) |
| X = I | (28) |

(X = $CO_2H$)

TERTIARY ACIDS

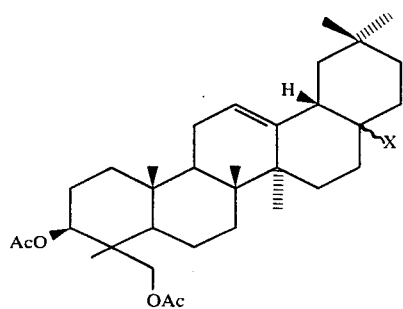

X = β-CO$_2$H (29)
X = H (30)

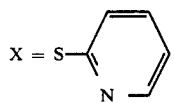

X = S-pyridyl (31)

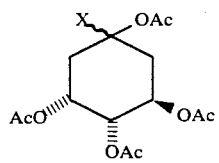

X = β-CO$_2$H (32)
X = H (33)

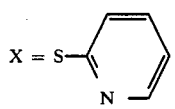

X = S-pyridyl (34)

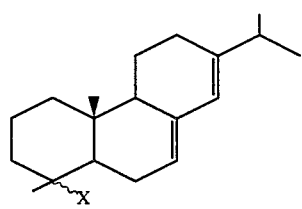

X = α-CO$_2$H (35)
X = H (36)

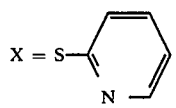

X = S-pyridyl (37)

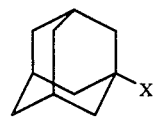

X = CO$_2$H (38)
X = H (39)

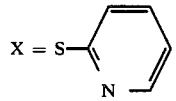

X = S-pyridyl (40)

X = Cl (41)

-continued
TERTIARY ACIDS

X = Br (42)
(X = CO$_2$H)

The process which is the subject of the present invention will be described below in greater detail with reference to a few particular examples in which it has been used, which have been grouped together according to the particular type of application and for which the scheme of the reaction mechanism will be shown each time.

EXAMPLES 1 TO 11

Supplying thermal and/or photochemical energy to the thionopyridone ester of general formula (II) leads to the formation of carbon-containing free radicals according to Scheme 1 restated below:

Scheme 1

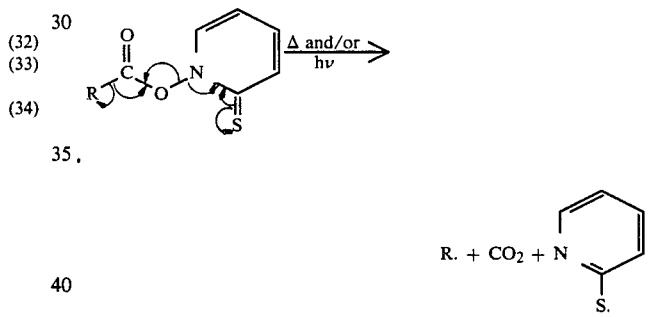

There then occurs, always as a result of supplying energy, a decarboxylative rearrangement of the N-acyloxy-2-pyridone of formula (II), in accordance with Scheme 2 below:

Scheme 2

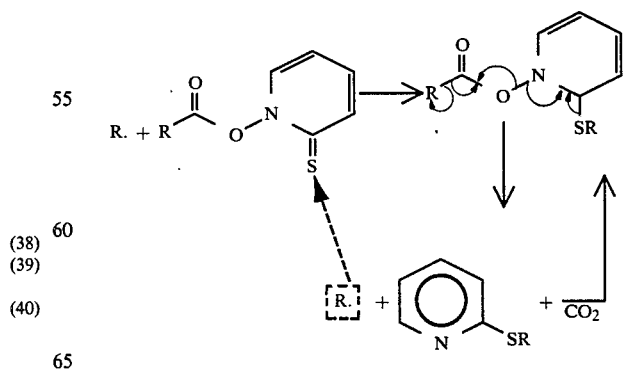

This free radical chain reaction leads to the formation of the corresponding pyridyl sulfide.

EXAMPLE 1

Preparation of 1,3,4,5-tetraacetoxy-1-(2'-pyridyl)mercaptocyclohexane

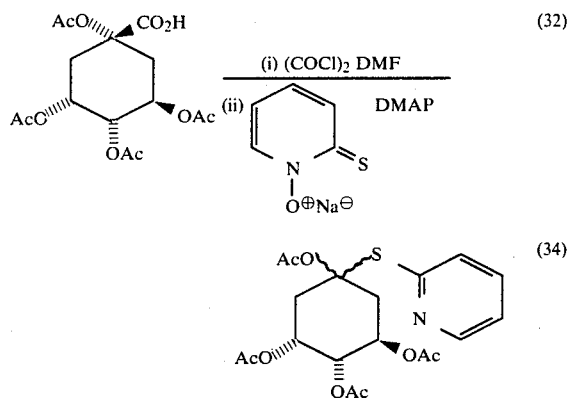

360 mg (1 mmol) of peracetoquinic acid (32) are taken into solution with stirring in 5 ml of benzene with the addition of 1 ml of oxalyl chloride and 1 drop of DMF for 3 hours. After evaporation to dryness, the residue is taken up in 5 ml of benzene and added with stirring to a suspension of 180 mg (1.1 mmol) of the sodium salt of N-hydroxypyridine-2-thione and 12 mg (0.1 mmol) of DMAP. The reaction mixture is kept refluxing in 10 ml of toluuene under an atmosphere of nitrogen. After 2 hours of heating under reflux, the cooled reaction mixture is filtered on Celite and evaporated to dryness. By flash chromatography on silica (90% of $CH_2Cl_2$; 10% EtOAc), 306 mg of pyridyl sulfide of formula (34) are obtained in the form of a yellowish oil. Yield 72%.

$\delta$(400 MHz $CDCl_3$): $\delta$2.00-2.13, 8 separate 3H singlets. 2.30 (1HM); 2.41 (2HM); 2.50 (2HM); 2.80 (1HM); 3.22 (1HM); 3.40 (1HM); 5.00 (1HM); 5.18 (1HM); 5.25 (1HM); 5.28 (1HM); 5.36 (1HM); 5.57 (1HM); 7.25 (2HM); 7.43 (2HM); 7.62 (2HM); 8.55 (2HM).

$\nu(CH_2Cl_2)cm^{-1}$ 1700, 1720-1740 broad m/e 425 $(M^{+0.7})$.

$\lambda max^{nm}$ 250 (4300), 284 (3600).

$[\alpha]_D^{18} -100°$ (C=1 in $CHCl_3$).

$C_{19}H_{23}NO_8S$; found: C 53.89; H 5.71; N 3.15; S 7.41%. calculated: C 53.64; H 5.44; N 3.29; S 7.54%.

EXAMPLE 2

Working in the same manner as in Example 1, the following reaction is carried out:

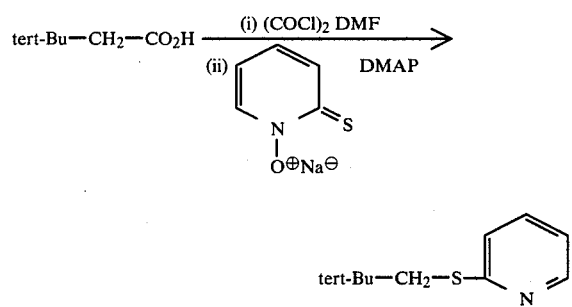

By maintaining the temperature of the reaction medium at 130° C. for 1 and half hours, the pyridyl sulfide is obtained in 78% yield.

EXAMPLE 3

Working in the same manner as in Example 1, the following reaction is carried out:

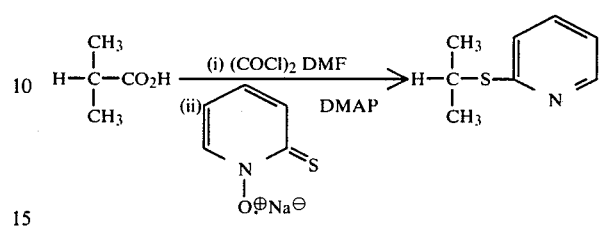

By maintaining the temperature of the reaction medium at 80° C. for 2 and half hours, the pyridyl sulfide is obtained in 78% yield.

EXAMPLE 4

Working in the same manner as in Example 1, the following reaction is carried out:

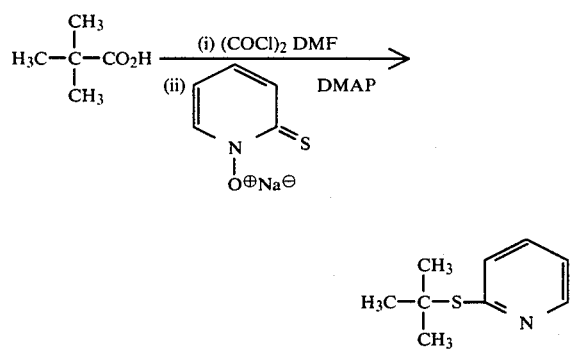

By maintaining the temperature of the reaction medium at 80° C. for 1 and half hours, the pyridyl sulfide is obtained in 71% yield.

EXAMPLE 5

Preparation of 3α-acetoxy-11-oxo-23-(2'-pyridyl)mercapto-24-norcholane 432 g (1 mmol) of acetyl-11-oxolithocholic acid are added into 5 ml of benzene with 1 ml of oxalyl chloride and 1 drop of DMF, and the mixture is maintained stirred for 3 hours. After evaporating to dryness, the residue is taken up in 5 ml of toluene and added with stirring to a suspension of 180 mg (1.1 mmol) of the sodium salt of N-hydroxypyridine-2-thione and 12 mg (0.1 mmol) of DMAP. The reaction mixture is kept refluxing in 10 ml of toluene under an atmosphere of nitrogen. After one and a half hours of heating under reflux, the cooled reaction mixture is filtered and evaporated to dryness. By flash chromatography on silica (100% $CH_2Cl_2$), 382 mg of the pyridyl sulfide of formula (14) are obtained in the form of a yellow oil which does not crystallize.

Yield 77%.

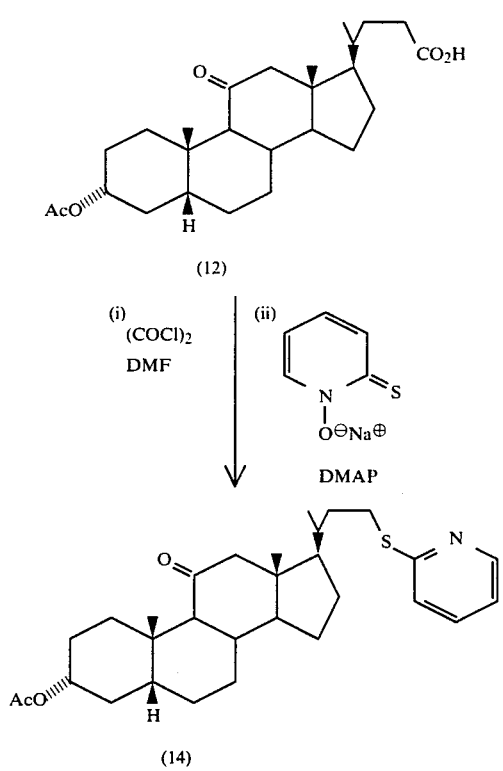

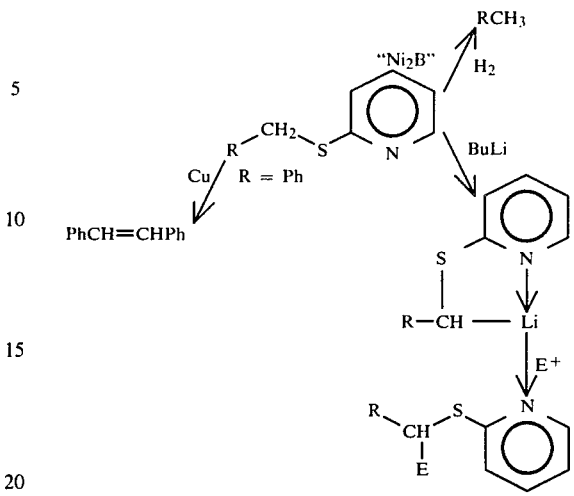

δ(400 MHz CDCl$_3$) 0.65 (3H s); 1.00 (3H d, J=7 Hz); 1.18 (3H s); 2.03 (3H s); 2.28 (1H d, J=10 Hz); 2.40 (1H d, J=10 Hz); 2.55 (2H m); 3.06 (1H m); 3.30 (1H m); 4.72 (1H m); 6.95 (1H dd, J$_1$ =9 Hz, J$_2$=6 Hz); 7.15 (1H d, J$_3$=10 Hz); 7.37 (1H dd, J$_3$=10 Hz, J$_1$=9 Hz); 8.40 (1H d, J$_2$=6 Hz).

ν(CH$_2$Cl$_2$) cm$^{-1}$ 1700, 1720, 1575, 1550.

m/e 497 (M$^{+0.7}$).

[α]$_D^{18}$ +60° (C=0.9 in CHCl$_3$).

λ$_{max}$ (EtOH) 253 nm (7980); 292 nm (2900).

C$_{23}$H$_{43}$NO$_2$S: found: C 72.02; H 8.58; N 2.58. calculated: C 72.39; H 8.71; N 2.81.

By working in the same manner as in Example 5 above, a number of reactions of the same type are carried out on various other acids. The experimental conditions, yield and nature of the products are recorded in the table below:

| Example | Acid | Temperature (°C.) | Time (hour) | Product obtained | Yield (%) |
|---|---|---|---|---|---|
| n° 6 | (1) | 80 | 2 | (3) | 92 |
| n° 7 | (7) | 110 | 2 | (9) | 74 |
| n° 8 | (16) | 110 | 2,5 | (18) | 74 |
| n° 9 | (20) | 110 | 1,5 | (22) | 98 |
| n° 10 | (29) | 80 | 1 | (31) | 74 |
| n° 11 | (35) | 80 | 3 | (37) | 71 |

The various pyridyl sulfides thus obtained are also useful as synthesis intermediates, as described for example by Mukaiyama et al. in Chem. Letts., 1159 (1975) and Chem. Letts., 259 (1972).

The various applications of the pyridyl sulfides can be schematized as follows.

EXAMPLES 12 TO 22

The carbon-containing free radicals R. obtained in accordance with Scheme 1 react with tri-n-butylstannane in accordance with Scheme 3 below to lead to the decarboxylated compound of formula RH:

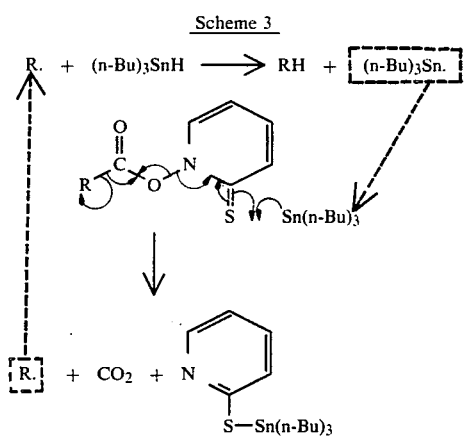

Scheme 3

EXAMPLE 12

Preparation of n-heptadecane

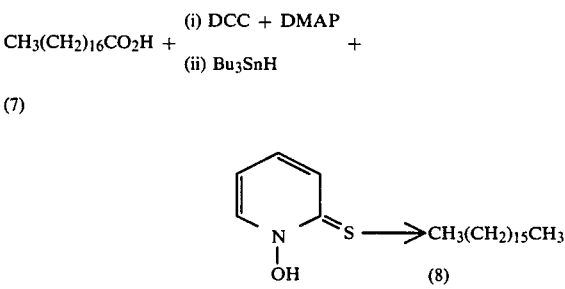

286 mg (1 mmol) of stearic acid (7) are mixed with 151 mg (1.2 mmol) of N-hydroxypyridine-2-thione, 183 mg (1.5 mmol) of p-dimethylaminopyridine (DMAP) and 310 mg (1.5 mmol) of dichlorohexylcarbodiimide (DCC). The mixture in 20 ml of benzene is stirred under an atmosphere of nitrogen and the solution obtained is brought to reflux so as to distil 10 ml of benzene. After 45 minutes under reflux, 10.8 ml (3 mmol) of tri-n-butylstannane and 10 mg of azobis(isobutyronitrile) (AIBN) in 10 ml of benzene are added dropwise during 15 minutes. Heating under reflux is continued for 6 hours, 10 ml of carbon tetra-chloride are then added, and refluxing is continued for one hour before evaporating the mixture to dryness. The residue is treated with iodine (20% in 10 ml $CH_2Cl_2$) and potassium fluoride (10% in 10 ml $H_2O$), and the two phases are then vigorously stirred for 10 minutes. The polymeric tin residues are filtered under vacuum on Celite and washed with 5 ml of dichloromethane. The organic phase is removed and the aqueous layer is extracted twice with dichloromethane (2×10 ml). The combined organic phases are washed with sodium thiosulfate (10%, 10 ml) and 10 ml of water, dried over sodium sulfate, filtered and evaporated to dryness. The crude product purified by filtration on silica gel (100% pentane) gives 228 mg of n-heptadecane (8).

Yield 95%. M.p.=22° C.

EXAMPLE 13

Preparation of 3β,24-diacetoxynor-28-olean-12-ene

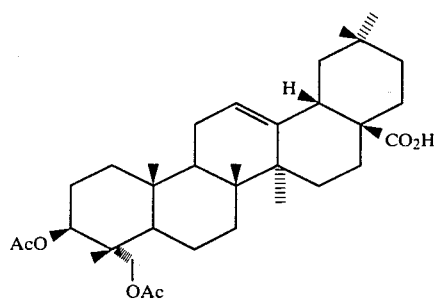

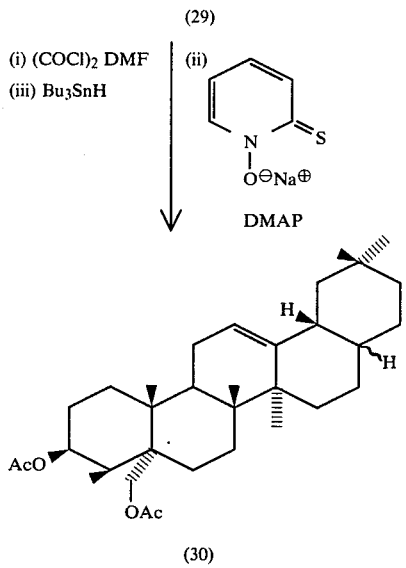

556 mg (1 mmol) of hederagenin diacetate (29) are mixed into 5 ml of benzene with 1 ml of oxalyl chloride. After addition of a drop of DMF, stirring is continued for 3 hours and the mixture is evaporated to dryness. The residue is taken up in 5 ml of benzene and added dropwise and with stirring during 10 minutes to a suspension of 223 mg (1.5 mmol) of sodium salt of N-hydroxypyridine-2-thione and 12 mg (0.1 mmol) of DMAP. The reaction mixture is kept refluxing in 10 ml of benzene under an atmosphere of nitrogen. Refluxing is continued for 2 hours before adding, dropwise during 10 minutes, 2 mmol of tri-n-butylstannane and 10 mg of AIBN in 5 ml of benzene. After 2 hours' further refluxing, 10 ml of carbon tetrachloride are added and refluxing is continued for 1 hour before evaporation to dryness. The residue is treated overnight with iodine (20% in $CH_2Cl_2$, 10 ml) and potassium fluoride (10% in water, 10 ml). The polymeric products are filtered under vacuum. The aqueous phase is extracted twice with dichloromethane (2×10 ml) and the combined organic phases are washed with sodium thiosulfate (10%, 10 ml) and with 10 ml of water, and then dried over sodium sulfate. The mixture is filtered and evaporated to dryness. After filtration of the crude product on silica (eluant: 75% pentane, 25% ether), 444 mg of compound (30) are obtained. Yield 86%.

M.p. 114°–115° C. (MdOH).

$[\alpha]_D^{16}+80°$ (C=1 in $CHCl_3$).

$\nu$(Nujol)$cm^{-1}$ 1740, 1730.

m/e 512 M+.), 452 (M-60), 512 452 (M* 399.0).

δ(400 MHz in $CDCl_3$) 0.89 (3H s); 0.925 (6H s); 0.95 (3H s); 1.05 (3H s); 1.09 (3H s); 2.08 (3H s); 2.13 (3H s); 2.40 (1H m); 3.73 (1H d, J=8 Hz); 3.91 (1H d, J=8 Hz); 4.81 (1H m); 5.13 (1H s).

$C_{33}H_{52}O_4$: found: C 77.38; H 10.11. calculated: C 77.30; H 10.23.

By working in the same manner as in Example 13 above, a number of reactions of the same type are carried out on various other acids. The experimental conditions, yield and nature of the products are recorded in the table below:

| Example | Acid | Temperature (°C.) | Time (hour) | Product obtained | Yield (%) |
|---|---|---|---|---|---|
| n° 14 | (1) | 80 | 0.5 | (2) | 72 |
| n° 15 | (10) | 80 | 6 | (11) | 91 |
| n° 16 | (12) | 80 | 6 | (13) | 77 |
|  |  |  |  | (14) | 20 |
| n° 17 | (16) | 80 | 6 | (17) | 92 |
| n° 18 | (20) | 60 | 3 | (21) | 48 |
|  |  |  |  | (22) | 39 |
| n° 19 | (20) | 40 | 6 | (21) | 72 |
|  |  |  |  | (22) | 15 |
| n° 20 | (35) | 80 | 3 | (36) | 65 |
| n° 21 | (32) | 110 | 0.33 | (33) | 73 |

Comment

It has been shown that, when the temperature of treatment of the esters derived from primary and secondary acids is raised, competition is induced between the two types of reaction mechanisms mentioned earlier. This is especially evident when reading Examples nos. 18 and 19. Raising the temperature leads to increased formation of the corresponding pyridyl sulfide derivative. The formation of the latter can be reduced, or even eliminated, by lowering the temperature and/or the reaction time. In any case, the pyridyl sulfide can be readily reduced to the corresponding noralkane, for example by reduction by means of Raney nickel.

The various types of decarboxylation in the presence of stannane are illustrated by the reaction scheme below:

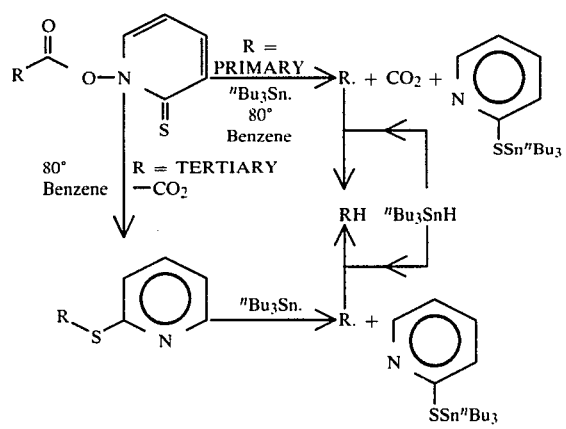

R = PRIMARY, SECONDARY, 110°, Toluene ⟶

BOTH PROCESSES TOGETHER

EXAMPLE 22

Preparation of n-heptadecane $CH_3(CH_2)_{16}CO_2H$ +

(7)

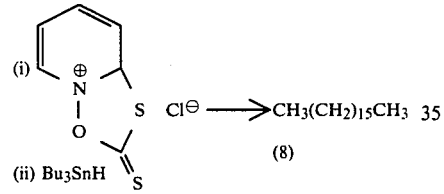

140 mg (1.1 mmol) of N-hydroxypyridine-2-thione in 5 ml of benzene are added dropwise at room temperature under an atmosphere of nitrogen to a solution of 120 mg (1.2 mmol) of phosgene in 5 ml of benzene, and this leads to the instantaneous precipitation of a white solid. 286 mg (1 mmol) of stearic acid and 0.5 ml of pyridine are added in 5 ml of benzene, and the reaction medium is taken to reflux for 4 hours. 3 mmol of tri-n-butylstannane in 5 ml of benzene with 10 mg of AIBN are added to the reaction medium during 10 minutes and refluxing is maintained for 2 and half hours. The reaction is carried out in the presence of tetrachloromethane, iodine and potassium fluoride, as indicated earlier. By filtration on silica (100% pentane), 168 mg of n-heptadecane are obtained. Yield 70%.

M.p. 22° C.

Comment

Isolation of the derivative of formula

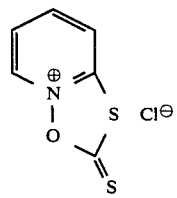

3.15 g (25 mmol) of N-hydroxypyridine-2-thione in 10 ml of benzene are added dropwise to a saturated solution of phosgene in 40 ml of benzene during 30 minutes at 0° C. The white precipitate obtained is filtered by means of a waterpump, rinsed with a small quantity of benzene and dried under vacuum at 50° C. for 6 hours. 4.40 g of an amorphous white powder are thus obtained.

Yield 98%.

M.p. 108°–110° C.

$\nu(Nujol)^{cm-1}$ 1770.

$C_6H_4ClNO_2S$: found: C 38.26; H 2.26; N 7.48; S 17.00; Cl 18.95. calculated: C 38.01; H 2.13; N 7.39; S 16.91; Cl 18.70.

EXAMPLES 23 TO 27

The carbon-containing free radicals R. obtained in accordance with Scheme 1 react with tert-butylmercaptan in accordance with Scheme 4 below, to lead to the decarboxylated compound of formula RH:

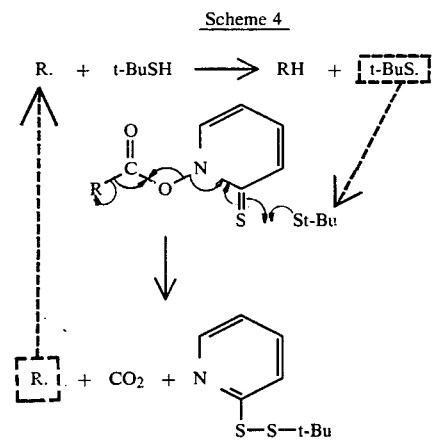

EXAMPLE 23

Preparation of 3β-acetoxy-11-oxo-5α-pregnane

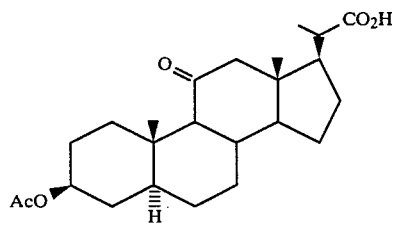

(i) (COCl)₂ DMF  (ii)
(iii) t-Bu—SH

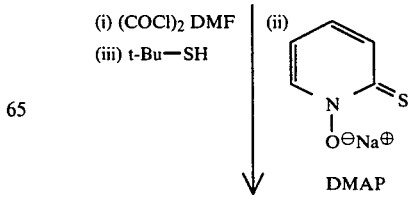

DMAP

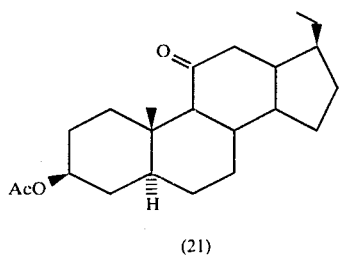

(21)

202 mg (0.5 mmol) of 3β-acetoxybis(nor)allocholanic acid in 5 ml of benzene are treated with 0.5 ml of oxalyl chloride and 1 drop of DMF at room temperature for 3 hours. After evaporation to dryness, the residue is taken up in 5 ml of toluene and added with stirring to a suspension of 90 mg (0.55 mmol) of sodium salt of N-hydroxypyridine-2-thione and 6 mg (0.05 mmol) of DMAP in 5 ml of toluene, which is refluxing under an atmosphere of nitrogen. Refluxing is maintained for 1 hour before the mixture is poured into 10 ml of a potassium carbonate solution. The organic phase is washed twice with saturated potassium carbonate (2×10 ml), once with water, then with dilute hydrochloric acid (3×10 ml) and finally with water before it is dried over sodium sulfate, filtered and evaporated. The crude product is filtered on silica (100% CH₂Cl₂) to give 147 mg of compound (21) which takes the form of a white crystalline solid.

Yield 82%.

M.p. 160° C.

EXAMPLE 24

By working as in Example 23, the reaction: (1)→(2) is carried out with a yield of 72%.

EXAMPLE 25

Preparation of 3α,12α-diacetoxy-24-norcholane

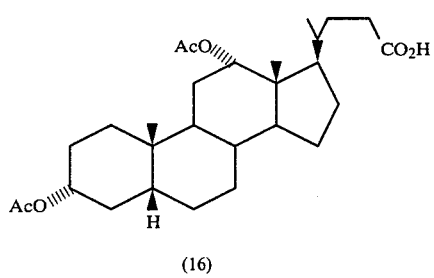

(16)

(i) (COCl)₂ DMF
(iii) t-Bu—SH (ii)

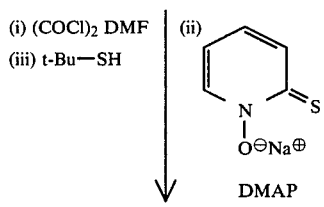

DMAP

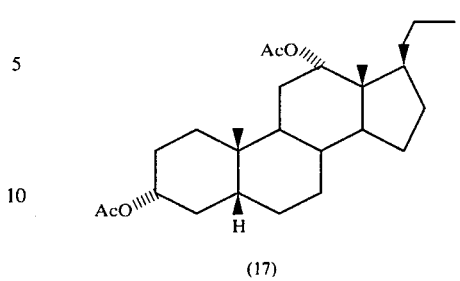

(17)

476 mg (1 mmol) of diacetyldeoxycholic acid are mixed in 5 ml of benzene with 1 ml of oxalyl chloride and 1 drop of DMF for 3 hours. After evaporation to dryness, the residue is taken up in 5 ml of benzene and added with stirring to a suspension of 180 mg (1.1 mmol) of sodium salt of N-hydroxypyridine-2-thione, 12 mg (0.1 mmol) of DMAP and 1 ml of t-butylmercaptan in 10 ml of toluene, which is refluxing under an atmosphere of nitrogen. The mixture is kept refluxing for 3 and half hours, before being poured into 10 ml of a saturated solution of potassium carbonate. The organic phase is again washed with a saturated solution of potassium carbonate (2×10 ml), 10 ml of water, twice 10 ml of HCl (2N) and finally with 10 ml of water before being dried over sodium sulfate, filtered and evaporated to dryness. The crude product is filtered on silica (100% CH₂Cl₂) to give 321 mg of the compound (17) which takes the form of a colorless oil.

Yield 74%.

M.p. 116°–117°C.

By working in the same manner as in Example 25 above, the same reaction is carried out on two other acids. The experimental conditions, yield and nature of the products are recorded in the table below:

| Example | Acid | Temperature (°C.) | Time (hour) | Product obtained | Yield (%) |
|---|---|---|---|---|---|
| n° 26 | (12) | 80 | 3.5 | (13) | 62 |
| n° 27 | (29) | 80 | 3 | (30) | 85 |

EXAMPLES 28 TO 40

The carbon-containing free radicals R. obtained in accordance with reaction Scheme 1 react with the compound X—CCl₃ in accordance with Scheme 5 below, leading to the decarboxylated compound of formula R—X:

Scheme 5

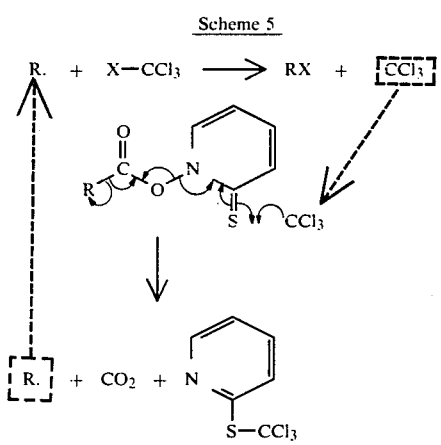

EXAMPLE 28

Preparation of 1-chloroadamantane

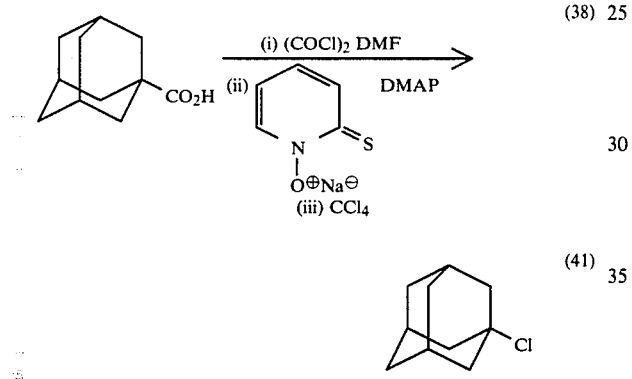

180 mg (1 mmol) of adamantane-1-carboxylic acid are mixed in 5 ml of benzene with 1 ml of oxalyl chloride and 1 drop of DMF for 3 hours. After evaporating to dryness, the crystalline residue is taken up in 5 ml of tetrachloromethane and added to a suspension of 180 mg (1.1 mmol) of sodium salt of N-hydroxypyridine-2-thione and 12 mg (0.1 mmol) of DMAP in 10 ml of tetrachloromethane, which is refluxing under an atmosphere of nitrogen. After 1 hour under reflux, the reaction mixture is cooled, filtered and evaporated to dryness before being filtered on silica (100% pentane). The product is sublimed (100° C., 15 minutes) to give 150 mg of compound (41) which takes the form of colorless crystals. Yield 88%. M.p. 165° C. (in a sealed tube).

By working in the same manner as in Example 28 above, the same reaction is carried out on other acids.

| Example | Acid | Chloride obtained | Yield (%) |
|---|---|---|---|
| n° 29 | (1) | (4) | 72 |
| n° 30 | (16) | (19) | 95 |
| n° 31 | (23) | (26) | 72 |
| n° 32 | Pivalic acid | (CH$_3$)$_3$—C—Cl | 82 |

EXAMPLE 33

Preparation of 3α-acetoxy-23-bromo-11-oxo-24-norcholane

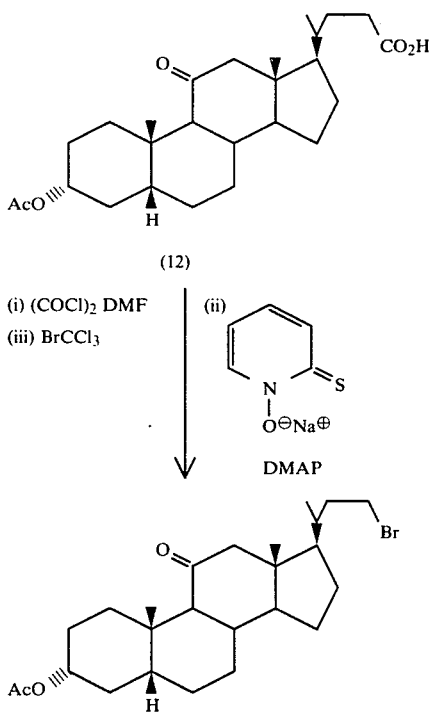

90 mg (0.2 mmol) of acetyl-11-oxolithocholic acid are mixed in 2 ml of benzene with 0.25 ml of oxalyl chloride and 1 drop of DMF for 3 hours. After evaporation to dryness, the residue is taken up in 5 ml of bromotrichloromethane and added to a suspension of 50 mg (0.3 mmol) of sodium salt of N-hydroxypyridine-2-thione and DMAP (trace) in 5 ml of bromotrichloromethane, which is refluxing under an atmosphere of nitrogen. Refluxing is maintained for 1 and half hours before the reaction mixture is cooled, filtered and evaporated to dryness. The crude product obtained is filtered on silica (100% CH$_2$Cl$_2$) to give 75 mg of the brominated derivative of formula (15). Yield 77%.

M.p. 164.5°–165° C.

δ(60 MHz CDCl$_3$) 0.66 (3H s); 1.20 (3H s); 2.00 (3H s); 2.40 (3H m); 3.40 (2H m); 4.70 (1H m).

m/e 466 (M$^{+0.7}$); 468 (M$^{+0.2}$).

ν(Nujol) cm$^{-1}$ 1730, 1720.

[α]$_D^{20}$+81° (C=0.3M CHCl$_3$).

C$_{25}$H$_{39}$BrO$_3$: found: C 63.97; H 8.35; Br 17.34%. calculated: C 64.23; H 8.41; Br·17.09%.

By working as in Example 33 above, the same reaction is performed on other acids.

| Example | Acid | Bromide obtained | Yield (%) |
|---|---|---|---|
| n° 34 | (1) | (5) | 95 |
| n° 35 | (12) | (15) | 98 |
| n° 36 | (23) | (27) | 90 |
| n° 37 | (38) | (42) | 98 |

EXAMPLE 38

Preparation of 1,3-diphenyl-2-iodopropane

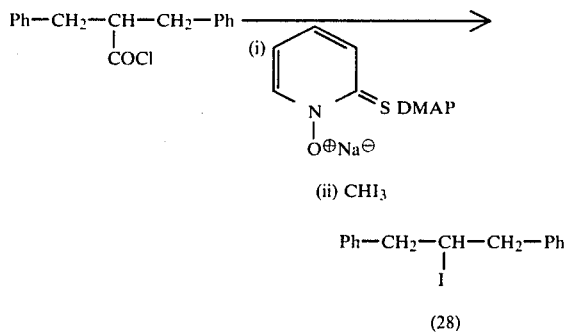

258 mg (1 mmol) of (dibenzyl)acetyl chloride in 1 ml of benzene are added with stirring to a suspension of 180 mg (1.1 mmol) of sodium salt of N-hydroxypyridine-2-thione, 12 mg (0.1 mmol) of DMAP and 433 mg (1.1 mmol) of iodoform in 10 ml of benzene, which is refluxing under an atmosphere of nitrogen. The reaction mixture is heated to reflux for 1 and half hours, and then cooled, filtered and evaporated to dryness. The crude product is filtered on silica (100% pentane) to give 194 mg of iodinated derivative of formula (28) which takes the form of a colorless oil. Yield 60%.

$\delta$(60 MHz CDCl$_3$) 3.20 (4H d, J=7 Hz); 4.38 (1H m, J=7 Hz); 7.25 (10H s).

m/e 322 (M$^{+0.7}$).

C$_{15}$H$_{15}$I: found: C 56.03; H 4.76%. calculated: C 55.92; H 4.69%.

Comment

In the absence of iodoform, the pyridyl sulfide derivative of formula (25) is obtained after 2 and half hours' refluxing, in a yield of 88%.

In a similar manner, the following iodinated derivatives are obtained:

| Example | Acid | Iodide obtained | Yield (%) |
|---|---|---|---|
| n° 39 | (1) | (6) | 74 |
| n° 40 | (23) | (28) | 60 |

EXAMPLE 41

Preparation of 1,3-diphenylpropan-2-ol

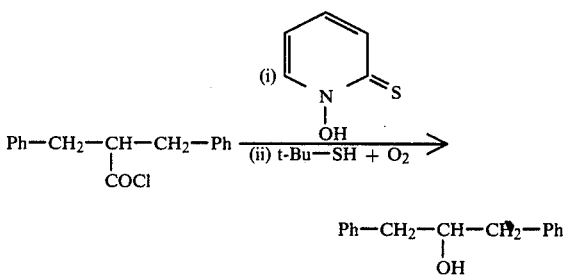

258 mg (1 mmol) of (dibenzyl)acetyl chloride in 1 ml of toluene are added at room temperature to 140 mg (1.1 mmol) of N-hydroxypyridine-2-thione and 0.1 ml of pyridine in 5 ml of toluene. The mixture is maintained with stirring for 30 minutes. The filtered solution is added dropwise during 20 minutes to 1 ml of t-butylmercaptan in 20 ml of toluene at 80° C., and a vigorous stream of oxygen is passed into this solution. The reaction is continued for 1 hour at 80° C., and the reaction mixture is then stirred for 2 hours at room temperature before being poured into 10 ml of a saturated solution of potassium carbonate. The organic phase is again washed twice with potassium carbonate (2×10 ml), then with 10 ml of water, twice with 10 ml of HCl (2N) and finally with twice 10 ml of water before being dried over sodium sulfate, filtered and evaporated to dryness. The crude product obtained is filtered on silica (100% CH$_2$Cl$_2$) to give 174 mg of the corresponding hydroxylated derivative. Yield 82%.

$\delta$(60 MHz CDCl$_3$) 2.80 (4H d, J=6 Hz); 4.33 (1H m, J=6 Hz); 7.25 (10 s).@.

$\nu$(CH$_2$Cl$_2$) cm$^{-1}$ 3600, 2900, 1595, 1570, 1485, 1070, 1020, 900.

m/e 212 M$^{+0.7}$.

EXAMPLE 42

By working in the same manner as in Example 41, the following reaction is carried out:

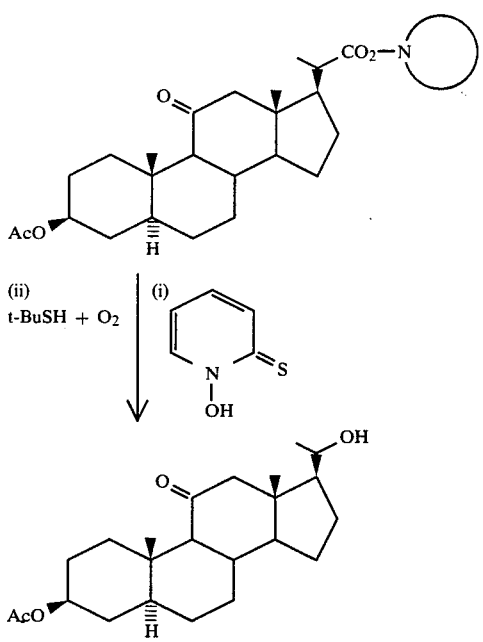

In this particular case, the hydroxylated compound is obtained in 85% yield by choosing a higher reaction temperature, which can be up to approximately 200° C. The nitrogen-containing heterocycle in position 23 can be a 1-piperidyl or 1-pyrrolidinyl radical. In this example, the attachment of the alcohol function is also performed after the formation of a carbon-containing free radical resulting from decarboxylation of a thiocarbonyl-containing ester of general formula (II).

It is clear that the present invention could not be limited to the particular examples mentioned above, and that it is perfectly possible to devise a number of variants of it without in any way departing from the scope of the invention. Thus, for example, it is possible to apply the process for the formation of carbon-containing free radicals R. to the reduction of anhydrides. In particular, the following reaction can be carried out:

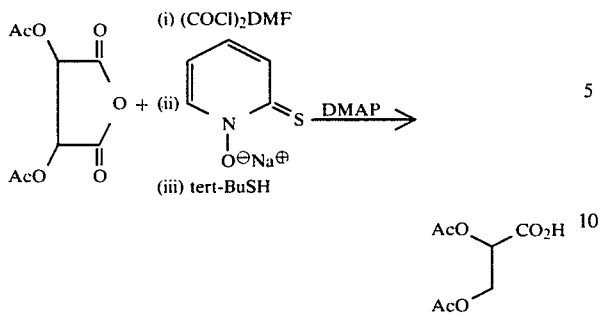

The above succinic anhydride derivative leads to the formation of an optically active glyceric acid which is especially useful in the synthesis of β-blockers.

By way of illustration of the application of the present invention to free radical polymerization, there will be mentioned below an example of homopolymerization of ethylene under high pressure in the presence of a catalyst consisting of the thiocarbonyl-containing ester corresponding to the formula:

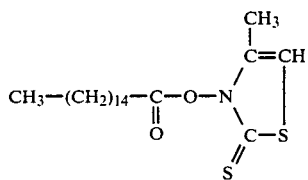

Polymerization of ethylene under high pressure

The polymerization reaction of ethylene is conducted with stirring in an autoclave of 1 liter capacity, under the following conditions:
pressure: 1500 bars
temperature: 155° C.
stirring: 1500 rpm.

The operations were carried out in the following order:
bringing the reactor to temperature
establishing the atmosphere of ethylene, then introduction of ethylene until a pressure of 1500 bars is obtained in the autoclave
stabilization of pressure and temperature
injection of the catalyst-reaction
recovery of the polymer.

The catalyst was dissolved in heptane, in the proportion of 3.25 g/liter.

This solution was injected into the reactor under pressure in successive small quantities until correct initiation of the reaction was obtained. A total volume of 19 cm$^3$ of catalytic solution was introduced, equivalent to 0.0647 g of ester or $0.165 \times 10^{-3}$ mole of ester.

The polymerization lasted 15 minutes with a temperature rise of 15° C.

At the end of the reaction, a 32 g quantity of polyethylene was collected, which represents a degree of conversion of ethylene of 6.5%.

Characteristics of the polymer obtained

Analysis of the polymer thus obtained led to the following results:
density: 0.929
melting point: 121° C.

$CH_3$/1000 C: 12.9
vinyl bond/1000 C: 0.04

It will be noted that the product thus prepared has a higher density than that obtained with a peroxide under the same conditions (0.920–0.924). Moreover, better crystallinity is observed.

Finally, the following example for the preparation of 2-trifluoromethylthiopyridine is given in view of illustrating the application of the present invention to the perfluoration.

Scheme of reaction

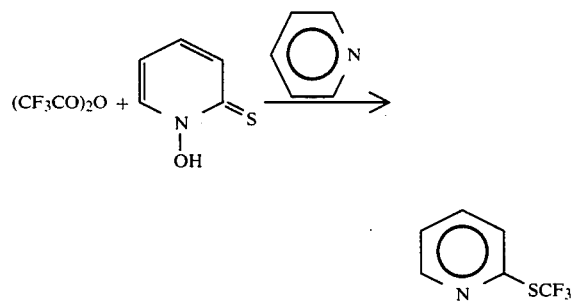

Procedure

To a solution of 2-mercaptopyridine N-oxide (0,2029 g) and pyridine (0.14 ml) in anhyd.ether (10 ml) was added trifluoroacetic anhydride (0.25 ml). The mixture was stirred at room temperature for 30 minutes under nitrogen, the time required for the esterification to be complete.

The mixture was then irradiated for 15 minutes with a tungsten lamp.

The pyridinium salt formed was eliminated by filtration on silica (solvent:ether) and the desired product purified by column chromatography (solvent:ether/pentane 50/50).

2-trifluoromethylthiopyridine[1] (0.28 g) was isolated with a yield of about 100%. The product was characterized by IR and NMR spectroscopy.

[1] Synthesis 1975/II/721-723 (L. M. YAGUPOLSKII).

We claim:

1. Process for the formation of carbon-containing free radicals R wherein thermal and/or photochemical energy is supplied to a thiocarbonyl-containing ester corresponding to the general formula (I):

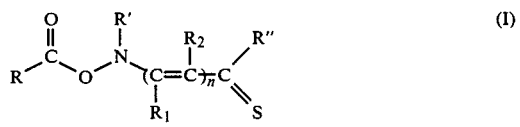

in which:
R denotes a saturated or unsaturated, linear or branched, aliphatic or aromatic, acyclic or alternatively mono- or poly-cyclic or mono- or poly-heterocyclic, carbon-containing radical;
R' and R" denote, independently of each other, an alkyl, alkenyl, aryl, aralkyl or alkaryl radical, or alternatively form together a 5- or 6-membered nitrogen-containing heterocycle which can also contain an additional heteroatom chosen from nitrogen and sulfur;

$R_1$ and $R_2$ denote, independently of each other, a hydrogen atom or a lower alkyl radical, and n is an integer equal to 0, 1, 2 or 3.

2. Process as claimed in claim 1, in which the said thiocarbonyl-containing ester is brought to a temperature which is substantially between 20° and 200° C.

3. Process as claimed in one of claims 1 or 2, in which the said thiocarbonyl-containing ester is subjected to irradiation with visible light.

4. Process according to claim 1, in which the said thiocarbonyl-containing ester is a thionopyridone ester corresponding to the general formula (II)

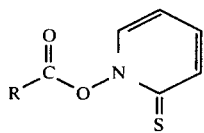

in which the radical R has the significance given in claim 1.

5. The process of claim 1 in which R includes at least one acetoxy group.

6. The process of claim 1 in which R includes at least one functional ketone.

7. The process of claim 2 in which said temperature is between 70° and 120° C.

* * * * *

UNITED STATES PATENT AND TRADEMARK OFFICE
CERTIFICATE OF CORRECTION

PATENT NO. : 4,668,356
DATED : May 26, 1987
INVENTOR(S) : Derek Harold Richard Barton, David Crich and William Branks Motherwell It is certified that error appears in the above-identified patent and that said Letters Patent is hereby corrected as shown below:

Top of column 5, the formulas at lines 9-13 should be raised to be to the right of the formulas at lines 2-7.

Column 4, lines 5 and 6, "n-Bu$_3$S., tert-BuS., CCl$_3$., CHI$_2$., R$_3$Sn., ArSO$_2$." should be --n-Bu$_3$S$^\bullet$, tert-BuS$^\bullet$, CCl$_3$$^\bullet$, CHI$_2$$^\bullet$, R$_3$Sn$^\bullet$, ArSO$_2$$^\bullet$--

Column 5, line 33, to the right of the heading "Primary Acids" add --(X=CO$_2$H)--.

Middle of column 8, the formulas at lines 36-41 should be raised to be to the right of the formulas at lines 29-34.

Column 8, lines 52 to 56, the formula to the right of the arrow should be

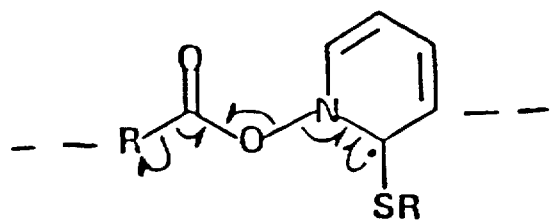

UNITED STATES PATENT AND TRADEMARK OFFICE
CERTIFICATE OF CORRECTION

PATENT NO. : 4,668,356
DATED : May 26, 1987
INVENTOR(S) : Derek Harold Richard Barton, David Crich and William Branks Motherwell It is certified that error appears in the above-identified patent and that said Letters Patent is hereby corrected as shown below:

The formula at column 9, lines 10-15; column 9, lines 55-60; column 10, lines 10-15; column 10, lines 28-33 and column 19, lines 27-32 should be changed from

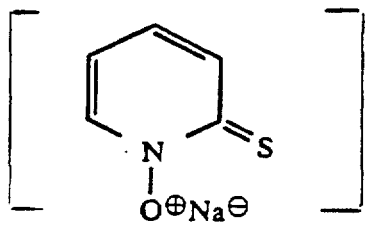

to

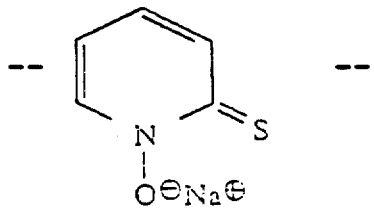

Column 13, lines 46 to 56, the formula should read:

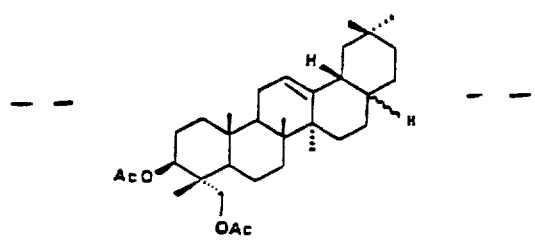

UNITED STATES PATENT AND TRADEMARK OFFICE
CERTIFICATE OF CORRECTION

PATENT NO. :  4,668,356

DATED : May 26, 1987

INVENTOR(S) : Derek Harold Richard Barton, David Crich and William Branks Motherwell It is certified that error appears in the above-identified patent and that said Letters Patent is hereby corrected as shown below:

Column 14, line 19, "MdOH" should be --MeOH--.

Column 14, line 23, "$M^+.$" should be --$M^+\cdot$--.

Column 15, line 6, below the arrow, "$^nBu_3Sn.$" should be --$nBu_3Sn\cdot$--.

Column 15, lines 30-38, left of arrow, formula should read:

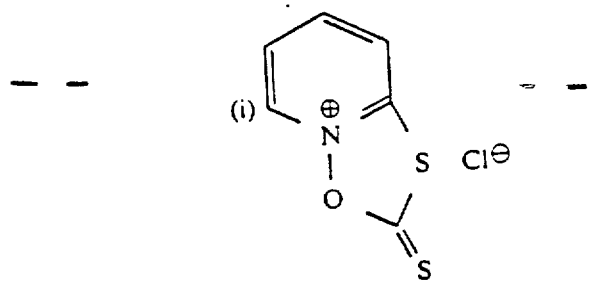

Column 19, line 4, " [CCl₃] " should be -- [ $\cdot CCl_3$ ] --

Column 19, line 10, " ⌒CCl₃ " should be -- ⌒$\cdot$ $CCl_3$ --

Signed and Sealed this

Eleventh Day of October, 1988

Attest:

DONALD J. QUIGG

Attesting Officer

Commissioner of Patents and Trademarks